(12) United States Patent
Scianamblo

(10) Patent No.: US 11,510,688 B2
(45) Date of Patent: Nov. 29, 2022

(54) BONE MATTER COLLECTION APPARATUSES

(71) Applicant: Michael J. Scianamblo, San Rafael, CA (US)

(72) Inventor: Michael J. Scianamblo, San Rafael, CA (US)

( * ) Notice: Subject to any disclaimer, the term of this patent is extended or adjusted under 35 U.S.C. 154(b) by 25 days.

(21) Appl. No.: 17/048,511

(22) PCT Filed: Apr. 18, 2019

(86) PCT No.: PCT/US2019/028177
§ 371 (c)(1),
(2) Date: Oct. 16, 2020

(87) PCT Pub. No.: WO2019/204644
PCT Pub. Date: Oct. 24, 2019

(65) Prior Publication Data
US 2021/0077125 A1  Mar. 18, 2021

Related U.S. Application Data

(60) Provisional application No. 62/659,558, filed on Apr. 18, 2018.

(51) Int. Cl.
*A61B 17/16* (2006.01)
*A61B 17/00* (2006.01)

(52) U.S. Cl.
CPC ...... *A61B 17/1635* (2013.01); *A61B 17/1615* (2013.01); *A61B 2017/00862* (2013.01);
(Continued)

(58) Field of Classification Search
CPC .............. A61B 7/1635; A61B 17/1615; A61B 2017/00862; A61B 2017/1602; A61B 17/1633; A61B 10/025
See application file for complete search history.

(56) References Cited

U.S. PATENT DOCUMENTS 2,930,264 A   3/1960   Lovert
3,384,085 A   5/1968   Hall
(Continued)

FOREIGN PATENT DOCUMENTS

CN   203029314   7/2013
EP   0120542   10/1984
(Continued)

OTHER PUBLICATIONS

International Search Report/Written Opinion issued by USPTO dated Jul. 5, 2019, 26 pages.
(Continued)

*Primary Examiner* — Matthew J Lawson
(74) *Attorney, Agent, or Firm* — Fish & Richardson P.C.

(57) ABSTRACT

This document describes bone matter collection devices and methods for their use. For example, longitudinally extendable/retractable spirally wound, conically-shaped bone matter collection/harvesting devices are described. In some implementations, such bone matter collection devices can be attachable with and detachable from bone drill bits. In some implementations, bone chips generated by bone drilling are collected in such a bone matter collection device while the bone matter collection device is detachably coupled to the bone drill bit, and the collected bone chips can be used for bone grafting and other purposes.

15 Claims, 4 Drawing Sheets

(52) U.S. Cl.
CPC ............... *A61B 2017/00969* (2013.01); *A61B 2017/00991* (2013.01)

(56) References Cited

U.S. PATENT DOCUMENTS

| | | |
|---|---|---|
| 3,400,617 A | 9/1968 | Sanborn |
| 3,583,821 A * | 6/1971 | Shaub ............... B23Q 11/0816 |
| | | 408/72 R |
| 3,824,026 A | 7/1974 | Gaskins |
| 3,936,213 A * | 2/1976 | Kappel ............... B23Q 11/0053 |
| | | 408/67 |
| 4,044,468 A | 8/1977 | Kalin |
| 4,190,386 A | 2/1980 | Brabetz et al. |
| 4,231,692 A | 11/1980 | Brabetz et al. |
| 4,332,561 A | 6/1982 | McSpadden |
| 4,353,698 A | 10/1982 | McSpadden |
| 4,456,411 A | 6/1984 | Clement |
| 4,457,710 A | 7/1984 | McSpadden |
| 4,536,159 A | 8/1985 | Roane |
| 4,538,989 A | 9/1985 | Apairo, Jr. et al. |
| 4,549,538 A * | 10/1985 | Schadrack, III ... A61B 17/1633 |
| | | 606/104 |
| 4,762,445 A | 8/1988 | Bunting et al. |
| 4,842,451 A | 6/1989 | Dugger |
| 4,884,980 A * | 12/1989 | Bensing ............... H01R 43/24 |
| | | 439/606 |
| 4,889,487 A | 12/1989 | Lovaas |
| 4,934,934 A | 6/1990 | Arpaio, Jr. et al. |
| 4,992,048 A | 2/1991 | Goof |
| 5,061,123 A * | 10/1991 | Broussard ............ B23Q 11/0053 |
| | | 408/67 |
| 5,106,298 A | 4/1992 | Heath et al. |
| 5,464,362 A | 11/1995 | Heath et al. |
| 5,498,158 A | 3/1996 | Wong |
| 5,503,554 A | 4/1996 | Schoeffel |
| 5,584,617 A | 12/1996 | Houser |
| 5,605,460 A | 2/1997 | Heath et al. |
| 5,653,561 A * | 8/1997 | May ............... B23Q 11/0046 |
| | | 408/67 |
| 5,658,145 A | 8/1997 | Maillefer et al. |
| 5,676,541 A | 10/1997 | Maillefer et al. |
| 5,713,736 A | 2/1998 | Heath |
| 5,716,736 A | 2/1998 | Heath et al. |
| 5,743,916 A | 4/1998 | Greenberg et al. |
| 5,752,825 A | 5/1998 | Buchanan |
| 5,772,367 A * | 6/1998 | Daniel ............... B23Q 11/0046 |
| | | 173/75 |
| 5,775,904 A | 7/1998 | Riitano |
| 5,836,764 A | 11/1998 | Buchanan |
| 5,842,862 A | 12/1998 | Nissan |
| 5,882,198 A | 3/1999 | Taylor et al. |
| 5,888,036 A | 3/1999 | Arai et al. |
| 5,897,274 A | 4/1999 | Ogura et al. |
| 5,897,316 A | 4/1999 | Buchanan |
| 5,902,106 A | 5/1999 | McSpadden |
| 5,921,775 A | 7/1999 | Buchanan |
| 5,938,440 A | 8/1999 | McSpadden |
| 5,980,166 A | 11/1999 | Ogura |
| 5,984,679 A | 11/1999 | Farzin-Nia et al. |
| 6,106,296 A | 8/2000 | Johnson |
| 6,146,066 A * | 11/2000 | Yelton ............... B23Q 11/0046 |
| | | 144/252.1 |
| 6,250,857 B1 | 6/2001 | Kersten |
| 6,299,445 B1 | 10/2001 | Garman |
| 6,315,558 B1 | 11/2001 | Farzin-Nia et al. |
| 6,419,488 B1 | 7/2002 | McSpadden et al. |
| 6,575,748 B1 | 6/2003 | Filhol |
| 6,702,579 B1 | 3/2004 | Hoppe et al. |
| 6,890,134 B1 | 5/2005 | Wagner et al. |
| 6,929,078 B1 | 8/2005 | Randall |
| 6,942,484 B2 | 9/2005 | Scianamblo |
| 7,094,056 B2 | 8/2006 | Scianamblo |
| 7,125,252 B2 | 10/2006 | Rouiller et al. |
| 7,175,371 B2 * | 2/2007 | Vidal ............... B23Q 11/0064 |
| | | 408/1 R |
| 7,717,710 B2 | 5/2010 | Danger et al. |
| 7,955,078 B2 | 6/2011 | Scianamblo |
| 8,206,067 B2 | 6/2012 | Turrini |
| 8,454,361 B2 | 6/2013 | Scianamblo |
| 8,496,476 B2 | 7/2013 | Scianamblo |
| 8,721,234 B2 * | 5/2014 | Santamarina ......... B23B 49/005 |
| | | 408/202 |
| 8,727,680 B2 | 5/2014 | Wada et al. |
| 8,740,513 B2 * | 6/2014 | Santamarina ......... B23B 49/005 |
| | | 408/67 |
| 8,882,504 B2 | 11/2014 | Scianamblo |
| 8,915,921 B2 * | 12/2014 | Ralph ................ A61B 17/1635 |
| | | 606/80 |
| 8,932,056 B2 | 1/2015 | Scianamblo |
| D750,246 S | 2/2016 | Scianamblo |
| 9,271,740 B2 | 3/2016 | Scianamblo |
| 9,277,925 B2 | 3/2016 | Scianamblo |
| 11,059,140 B2 * | 7/2021 | Buenaventura .... B23Q 11/0071 |
| 11,191,605 B2 * | 12/2021 | Dejardin ............... A61B 90/08 |
| 2002/0031745 A1 | 3/2002 | Kumar et al. |
| 2003/0159544 A1 | 8/2003 | Moser et al. |
| 2004/0023186 A1 | 2/2004 | McSpadden |
| 2004/0042865 A1 | 3/2004 | Oettle |
| 2004/0131993 A1 | 7/2004 | Rouiller et al. |
| 2004/0185414 A1 | 9/2004 | Badoz |
| 2004/0210229 A1 * | 10/2004 | Meller ................ A61B 10/025 |
| | | 606/80 |
| 2004/0219485 A1 | 11/2004 | Scianamblo |
| 2004/0253379 A1 | 12/2004 | Sugita et al. |
| 2004/0265775 A1 | 12/2004 | Maillefer et al. |
| 2005/0026109 A1 | 2/2005 | Buchanan |
| 2005/0117984 A1 | 6/2005 | Eason et al. |
| 2005/0266375 A1 | 12/2005 | Brock et al. |
| 2005/0282117 A1 | 12/2005 | Aravena et al. |
| 2006/0068362 A1 | 3/2006 | Desrosiers et al. |
| 2006/0111724 A1 | 5/2006 | Ping |
| 2006/0115339 A1 | 6/2006 | Wakui et al. |
| 2006/0115650 A1 | 6/2006 | Hanyu et al. |
| 2006/0228668 A1 | 10/2006 | McSpadden |
| 2006/0228669 A1 | 10/2006 | Scianamblo |
| 2007/0015107 A1 | 1/2007 | Mannschedel et al. |
| 2007/0059663 A1 | 3/2007 | Scianamblo |
| 2007/0082318 A1 | 4/2007 | Breguet |
| 2007/0184406 A1 | 8/2007 | Mason |
| 2008/0154150 A1 | 6/2008 | Goldenberg |
| 2009/0047080 A1 | 2/2009 | Schweigiofer et al. |
| 2010/0215450 A1 | 8/2010 | Santamarina et al. |
| 2010/0221078 A1 | 9/2010 | Borschert |
| 2011/0054483 A1 | 3/2011 | Howlett et al. |
| 2011/0144442 A1 * | 6/2011 | Farrell .................. A61B 1/32 |
| | | 600/206 |
| 2011/0236853 A1 | 9/2011 | Shimoo |
| 2011/0276029 A1 * | 11/2011 | Field ................... A61M 5/326 |
| | | 604/506 |
| 2012/0039680 A1 | 2/2012 | Koike et al. |
| 2012/0282571 A1 | 11/2012 | Ammon et al. |
| 2013/0170920 A1 | 7/2013 | Ogawa |
| 2013/0189644 A1 | 7/2013 | Johnson |
| 2013/0190560 A1 | 7/2013 | Kaneko et al. |
| 2016/0192945 A1 | 7/2016 | Scianamblo |
| 2016/0207121 A1 | 7/2016 | Scianamblo |
| 2018/0258979 A1 | 9/2018 | Omohundro et al. |

FOREIGN PATENT DOCUMENTS

| | | |
|---|---|---|
| EP | 0987076 | 3/2000 |
| EP | 1184004 | 3/2002 |
| EP | 1213074 | 6/2002 |
| EP | 1340573 | 9/2003 |
| FR | 2798277 | 3/2001 |
| FR | 2854054 | 10/2004 |
| FR | 2935260 | 3/2010 |
| JP | 52-156494 | 12/1977 |
| JP | 57-127608 | 8/1982 |
| JP | 62-241606 | 10/1987 |
| JP | H06-320323 | 11/1994 |
| JP | H11-19812 | 1/1999 |
| JP | 2002-144122 | 5/2002 |

(56) References Cited

FOREIGN PATENT DOCUMENTS

| JP | 2002-205213 | 7/2002 |
|----|-------------|--------|
| JP | 2007-0283473 | 11/2007 |
| SU | 637207 | 12/1978 |
| WO | WO 01/19279 | 3/2001 |
| WO | WO 02/065938 | 8/2002 |
| WO | WO 2004/098438 | 11/2004 |
| WO | WO 2009/001681 | 12/2008 |
| WO | WO 2014/118587 | 8/2014 |
| WO | WO 2014/118591 | 8/2014 |

OTHER PUBLICATIONS

U.S. Appl. No. 29/448,430, filed Mar. 12, 2013, Scianamblo.
dictionary.com, [online], "Straight, (n.d.). Dictionary.com Unabridged." Retrieved Feb. 11, 2010, from Dictionary.com website: http://dictionary.reference.com/browse/straight, 7pages.
merriam-webster.com [online], "Linear definition from Merriam-Webster on-line," Retrieved on Feb. 20, 2009, from http://www.merriam-webster.com/dictionary/linear, 3 pages.
tulsadentalspecialties.com [online] "Protaper Next". Dentsply Tulsa Dental Specialties. Last updated Dec. 5, 2014. Retrieved on Dec. 5, 2014. Retrieved from the internet: URC:<http://www.tulsadentalspecialties.com/default/endodontics_brands/PROTAPERNEXT.aspx>. 1 page.
YouTube [online], "Ultimate Handyman. Drilling Through Walls," Published Sep. 23, 2011. Retrieved on Nov. 11, 2014. Retrieved from URL<https://www.youtube.com/watch?v=fpFUxlcH2Lg>, 3 pages.
European Extended Search Report in European Appln. No. 19787670, dated May 14, 2021, 8 pages.

\* cited by examiner

BONE MATTER COLLECTION APPARATUSES

CROSS-REFERENCE TO RELATED APPLICATIONS

This application claims priority to U.S. Provisional Application Ser. No. 62/659,558 filed Apr. 18, 2018.

BACKGROUND

1. Technical Field

This document relates to bone matter collection devices and methods for their use.

2. Background Information

Osteotomies are routinely performed for surgical access or to divide or reposition a bone for surgical correction. Holes may be drilled in bones for various reasons, such as to accommodate screws, pins, dental implants and various other implantable devices and materials, or to collect a bone sample for biopsy.

SUMMARY

This document describes bone matter collection devices and methods for their use. For example, longitudinally extendable/retractable spirally wound, conically-shaped bone matter collection/harvesting devices are described herein. In some implementations, such bone matter collection devices can be attachable with and detachable from bone drills (e.g., the shank of a bone drill). In some implementations, bone chips generated by bone drilling are collected in such a bone matter collection device, while the bone matter collection device is detachably coupled to the bone drill, and the collected bone chips can be used for purposes such as, but not limited to, bone grafting.

In one aspect, this disclosure is directed to an apparatus for harvesting bone matter. The apparatus for harvesting bone matter includes a proximal end portion defining a proximal end opening that receives a shank of a drill, a distal end portion defining a distal end opening through which the drill can extend, and an intermediate section between the proximal and distal end portions. At least a portion of the intermediate section includes a spirally-wrapped ribbon member defining a frustoconical shape.

Such an apparatus for harvesting bone matter can optionally include one or more of the following features. The apparatus can be telescopic. The apparatus can be extendable and retractable between a longitudinally extended configuration and a longitudinally retracted configuration. The proximal and distal end portions are closer to each other while the apparatus is configured in the longitudinally retracted configuration as compared to while the apparatus is configured in the longitudinally extended configuration. The apparatus can be naturally-biased to be configured in the longitudinally extended configuration. The spirally-wrapped ribbon member can be longitudinally extended while the apparatus is configured in the longitudinally extended configuration and longitudinally retracted while the apparatus is configured in the longitudinally retracted configuration. The spirally-wrapped ribbon member can be naturally-biased to longitudinally extend such that the apparatus is configured in the longitudinally extended configuration. At least one wrap of the spirally-wrapped ribbon member can overlap a portion of a distally-adjacent wrap of the spirally-wrapped ribbon member and can be partially overlapped by a proximally-adjacent wrap of the spirally-wrapped ribbon member. The overlaps of adjacent wraps of the spirally-wrapped ribbon member can slidably increase when the apparatus reconfigures from a longitudinally extended configuration toward a longitudinally retracted configuration. The proximal end portion comprises a bearing or a bushing. The bearing can configure the apparatus to be rotatably coupleable with the drill. The proximal end portion can have a larger outer diameter than the distal end portion. The spirally-wrapped ribbon member can be made of an elastomer or can be metallic.

In another aspect, this disclosure is directed to a method of collecting bone matter. The method can include: releasably coupling a bone matter collection apparatus to a bone drill; drilling into bone matter using the bone drill while the bone matter collection apparatus is coupled to the bone drill (wherein bone chips generated by the drilling collect within an interior region defined by the spirally-wrapped ribbon member); after the drilling, decoupling the bone matter collection apparatus from the bone drill; and after the decoupling, obtaining at least some of the bone chips from the interior region. The bone matter collection apparatus can include a proximal end portion defining a proximal end opening that receives a shank of the bone drill, a distal end portion defining a distal end opening through which the bone drill can extend, and an intermediate section between the proximal and distal end portions. At least a portion of the intermediate section can include a spirally-wrapped ribbon member defining a frustoconical shape.

Such a method of collecting bone matter may optionally include one or more of the following features. The bone matter collection apparatus may be rotatably coupled to the bone drill such that during the drilling the bone drill rotates faster than the bone matter collection apparatus. During the drilling, the bone drill can be advanced into the bone matter and the bone matter collection apparatus can reconfigure to a shorter longitudinal length.

Particular implementations of the subject matter described in this document can be implemented to realize one or more of the following advantages. In some implementations, efficient removal of bone fragments improves cutting, visibility and offers an opportunity to capture bony fragments for reuse in an autograft. In some implementations, the bone matter harvesting devices disclosed herein are readily detachable from bone drills to facilitate convenient collection of bone chips contained within the bone matter harvesting device. The bone matter harvesting devices disclosed herein are convenient to manufacture and adaptable to work with most all implementations of drills and drill-like instruments. The bone harvesting devices can be reusable in some implementations, and the bone harvesting devices can be disposable in some implementations. The bone harvesting devices disclosed herein are also designed to collect bone matter efficiently while causing little or no interference to the drilling operation.

Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more implementations of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

During an osteotomy, fragments of bone matter can be detached or come loose. It would be desirable to collect such bone matter, either to simply ensure that it does not remain in the surgery site, or for use in grafting and other purposes. Accordingly, this document describes bone matter collection devices and methods for their use. For example, longitudinally extendable/retractable spirally wound, conically-shaped bone matter collection/harvesting devices are described herein. In some implementations, such bone matter collection devices can be attachable with and detachable from bone drill bits (e.g., the shank of a bone drill bit). In some implementations, bone chips generated by bone drilling are collected in such a bone matter collection device while the bone matter collection device is detachably coupled to the bone drill bit, and the collected bone chips can be used for bone grafting.

The bone matter collection devices described herein provide the opportunity to collect bone for an autograft, which is often necessary. In some cases, the surgeon may use an autograft from another site, or may elect to use allografts or artificial material. Autologous grafts, however, are preferable because they are inherently biocompatible, osteo-conductive, osteo-inductive, and osteogenic. Harvesting autologous bone from a donor site results in additional time and the attendant risk of complications such as donor site pain and morbidity. Allografts, derived from donor (cadaver) tissues, are only osteo-conductive, and may pose the risk of contamination. Artificial materials such as alloplastic bone cement are a poor choice for grafting since they are potentially antigenic and rarely osteo-conductive. Thus, bone collection from the original operating area is desirable.

Figure 2:
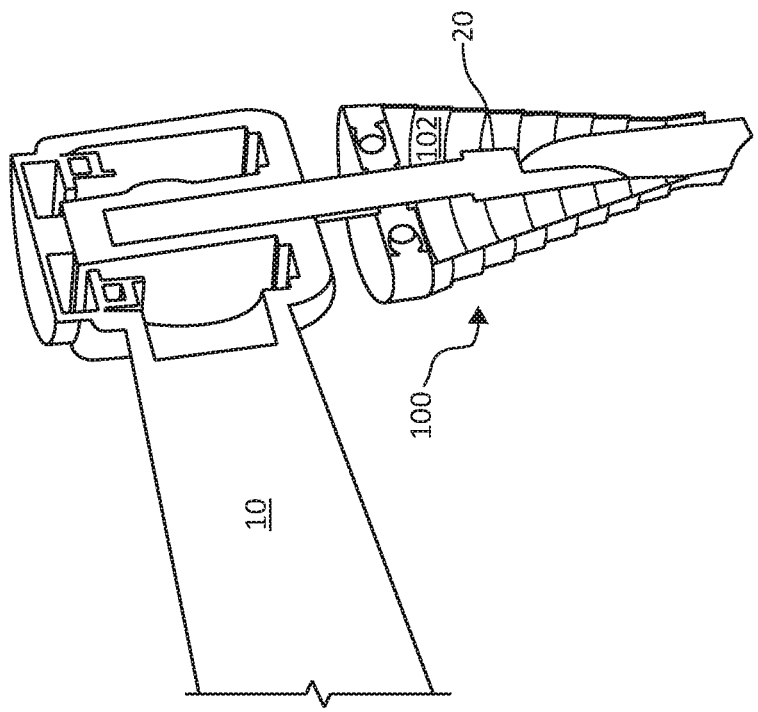
FIG. 2 is a cross-sectional view of the arrangement of FIG. 1.
Figure 1:
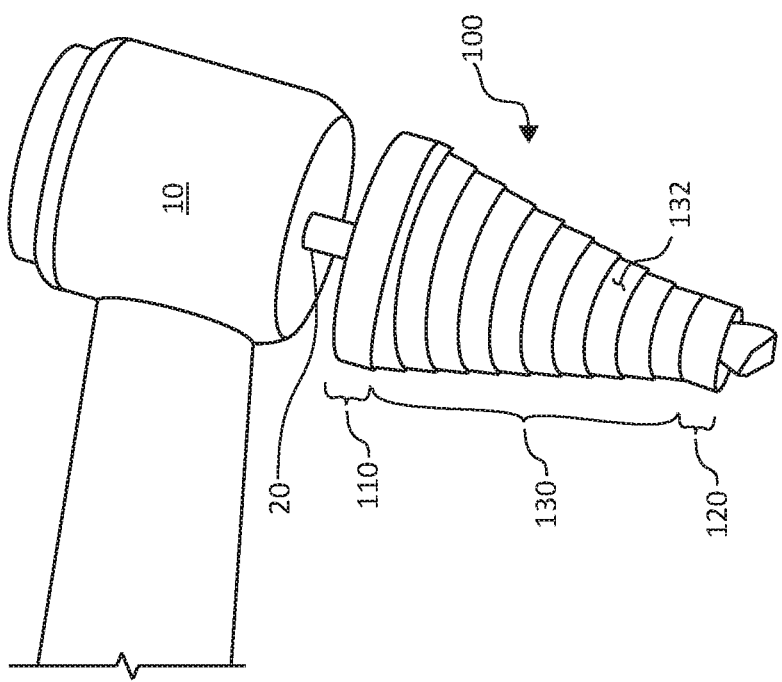
FIG. 1 illustrates a perspective view of a drilling device and a bone drill that is encompassed by an example bone matter collection device in accordance with some implementations.

Referring to FIGS. 1 and 2, an example apparatus 100 for bone matter harvesting (also referred to herein as bone matter collection) is shown, in conjunction with a drilling device 10 and a bone drill bit 20. The bone drill bit 20 is removably coupled to the drilling device 10. The drilling device 10 rotates the bone drill bit 20 about the longitudinal axis of the bone drill bit 20 in order to drill a hole in a bone matter. The bone matter collection device 100 is removably coupled to the bone drill bit 20.

The drilling device 10 depicted is only an example and is in no way limiting to the inventive concepts disclosed herein. The bone matter collection device 100 can be used with any and all types of suitable drilling devices. Similarly, the bone drill bit 20 depicted is only an example and is in no way limiting to the inventive concepts disclosed herein. The bone matter collection device 100 can be used with any and all types of suitable drills.

The bone matter harvesting apparatus 100 includes a proximal end portion 110, a distal end portion 120, and an intermediate section 130. The intermediate section 130 is located between the proximal end portion 110 and the distal end portion 120. In some implementations, the bone matter harvesting apparatus 100 is a unitary construct. In some implementations, the bone matter harvesting apparatus 100 comprises two or more components that are attachable and detachable from each other.

The proximal end portion 110 defines a proximal end opening that receives the shank of the bone drill bit 20. In some implementations, the proximal end portion 110 is releasably coupled to the shank of the bone drill bit 20 using a mechanical connection between the proximal end opening and the shank of the bone drill bit 20. The proximal end portion 110 can be a disk-shaped body having an opening in the center thereof.

The distal end portion 120 defines a distal end opening through which the bone drill bit 20 can extend. The proximal end portion 110 has a larger outer diameter than the distal end portion 120. The drilling device 10 is releasably coupled to the shank of the bone drill bit 20 and drives rotation of the bone drill bit 20.*hq*

At least a portion of the intermediate section 130 comprises a spirally-wrapped ribbon member 132. The spirally-wrapped ribbon member 132 is an elongated element that is wound multiple times around the central longitudinal axis of the bone matter harvesting apparatus 100. The ribbon member 132 is sufficiently thin that the ribbon can flex along the longitudinal direction of the drill 20. In some implementations, the spirally-wrapped ribbon member 132 is made of an elastomer. In some implementations, the spirally-wrapped ribbon member 132 is metallic.

Figure 6:
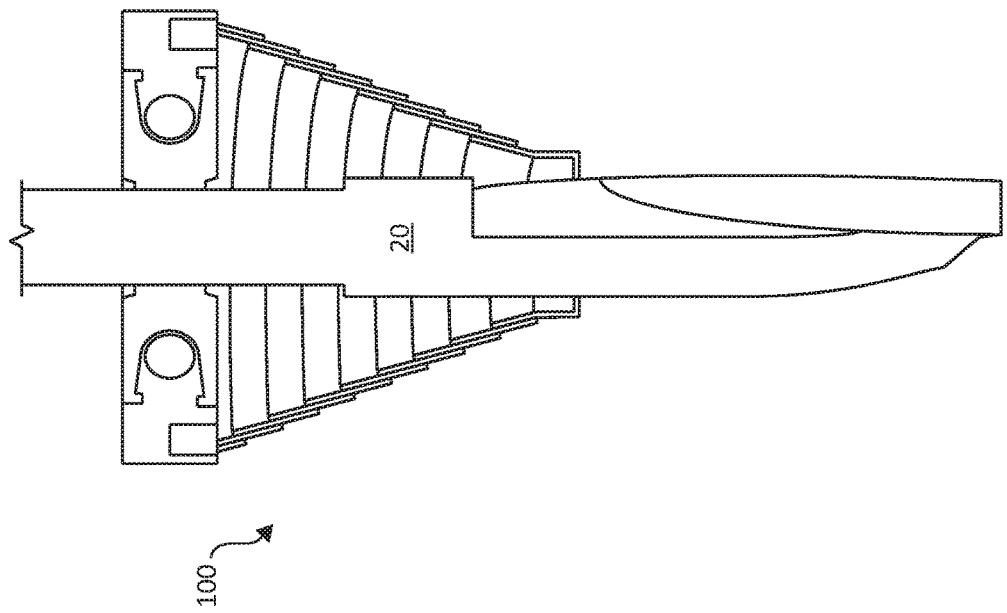
FIG. 6 shows a longitudinal cross-sectional view of the bone drill while encompassed by the bone matter collection device in a longitudinally retracted configuration.

Adjacent wraps or windings of the spirally-wrapped ribbon member 132 overlap each other. For example, at least one wrap of the spirally-wrapped ribbon member 132 overlaps a portion of a distally-adjacent wrap of the spirally-wrapped ribbon member 132, and is partially overlapped by a proximally-adjacent wrap of the spirally-wrapped ribbon member 132. As described further below, the overlaps of adjacent wraps of the spirally-wrapped ribbon member 132 slidably increase when the bone matter harvesting apparatus 100 reconfigures from a longitudinally extended configuration as shown, toward a longitudinally retracted configuration (as depicted in FIGS. 3 and 6).

In the depicted implementation, at least a portion of the spirally-wrapped ribbon member 132 defines a frustoconical shape along the intermediate section 130. The spirally-wrapped ribbon member 132 defines an interior space 102 (FIG. 2). The interior space 102 is used to receive and accumulate pieces of bone matter (e.g., chips, fragments, shavings, etc.) that result from the drilling of the bone drill bit 20 into bone matter. The spirally-wrapped ribbon member 132 can prevent bone matter from exiting from the sides of the interior space 102, and the proximal end portion 110 can prevent bone matter from exiting from the top of the interior space 102.

Figure 3:
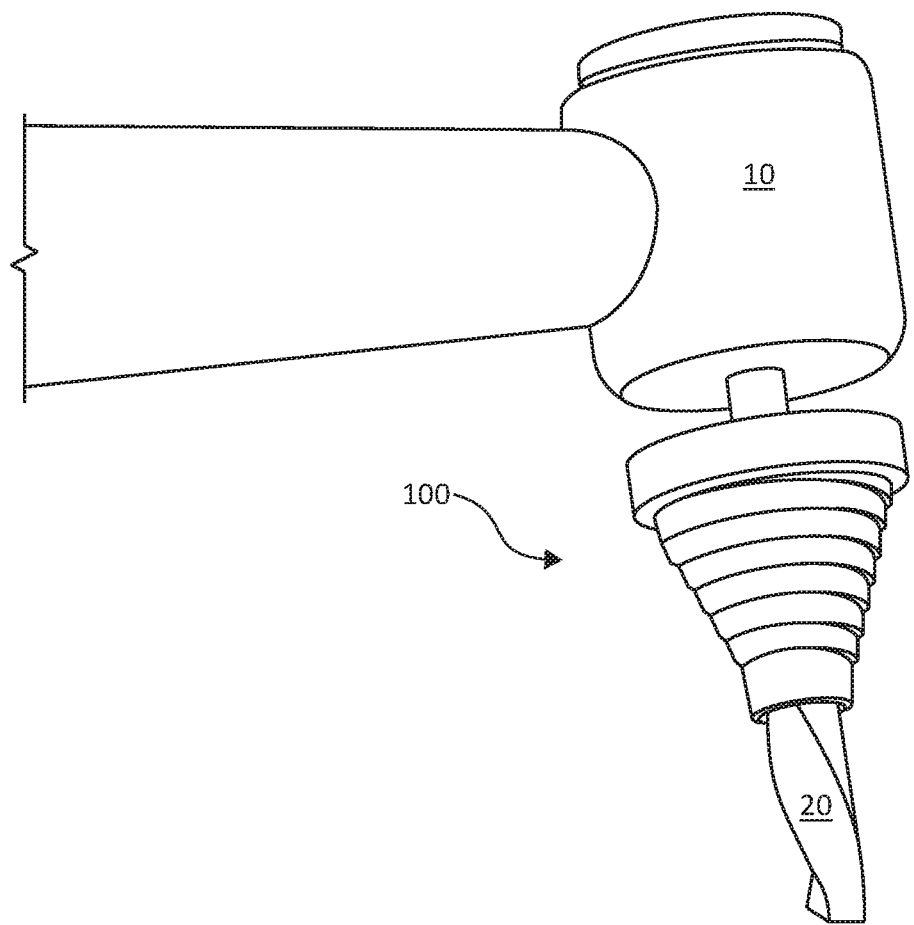
FIG. 3 illustrates another perspective view of the arrangement of FIG. 1 with the bone matter collection device in a longitudinally retracted configuration.

Referring also to FIG. 3, the bone matter harvesting apparatus 100 will reconfigure toward a longitudinally retracted configuration in response to advancement of the bone drill bit 20 into bone matter. That is, while the bone drill bit 20 is rotated by the drill 10 to cause the bone drill bit 20 to penetrate bone matter, the bone matter harvesting apparatus 100 will abut against the bone matter and will be thereby forced to longitudinally contract as the bone drill bit 20 advances.

As shown by a comparison of FIGS. 1 and 3, in FIG. 1 the bone matter harvesting apparatus 100 is in a longitudinally extended configuration and in FIG. 3 the bone matter harvesting apparatus 100 has reconfigured toward a longitudinally retracted configuration. Hence, the bone matter harvesting apparatus 100 is telescopic. The proximal end portion 110 and distal end portion 120 are closer to each other while the bone matter harvesting apparatus 100 is configured in the longitudinally retracted configuration as compared to while the bone matter harvesting apparatus 100 is configured in the longitudinally extended configuration.

In some implementations, the bone matter harvesting apparatus 100 is naturally-biased to be configured in the longitudinally extended configuration. For example, in some implementations the spirally-wrapped ribbon member 132 can have a shape memory such that the spirally-wrapped ribbon member 132 is naturally-biased to be configured in the longitudinally extended configuration. When the spirally-wrapped ribbon member 132 is forced to longitudinally compress/retract, the spirally-wrapped ribbon member 132 can naturally tend to rebound like a spring toward the longitudinally extended configuration.

Figure 4:
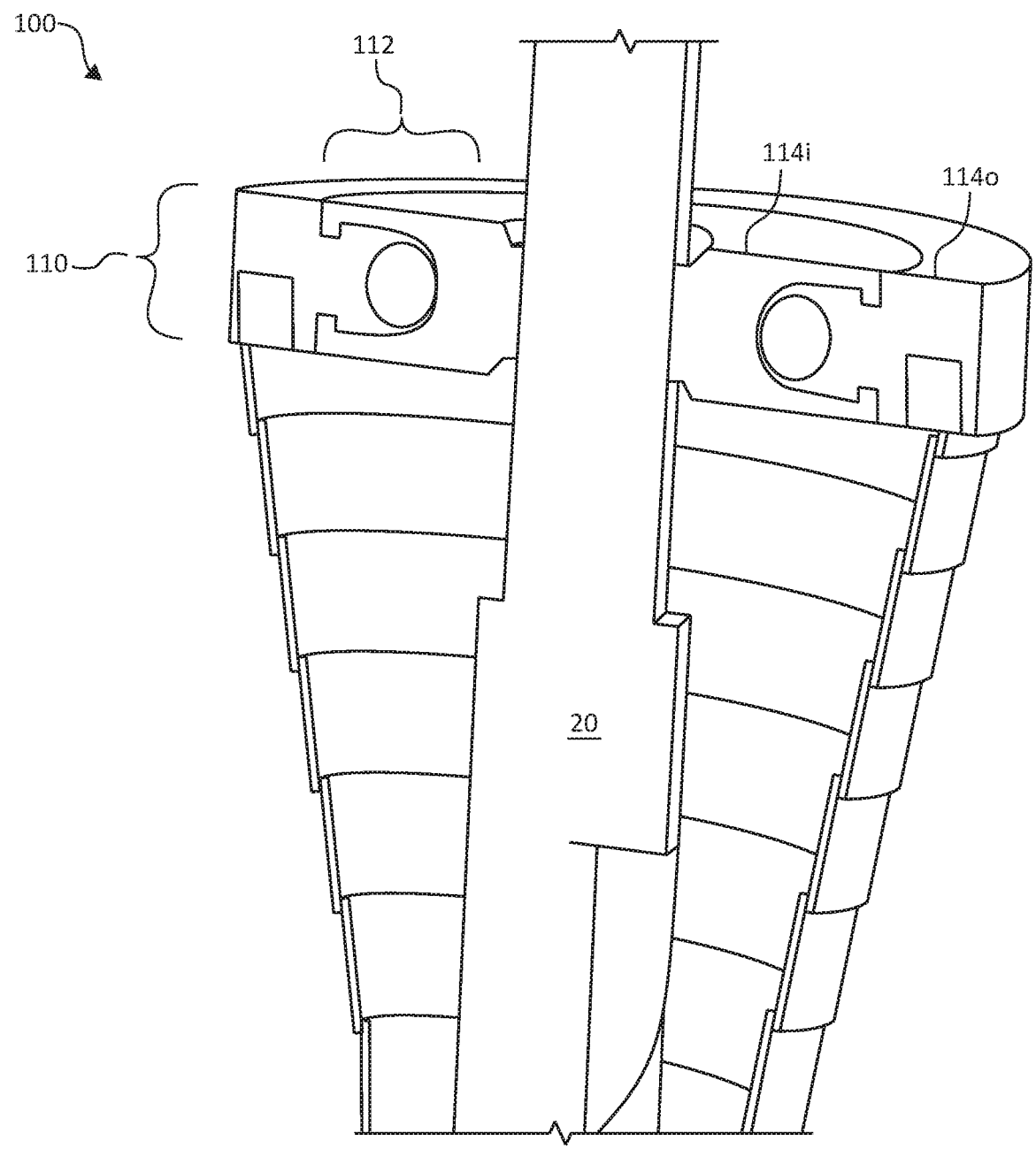
FIG. 4 is a cross-sectional perspective view showing an example of how the bone matter collection device can be rotatably and detachably coupled to the shank of the bone drill.

Referring also to FIG. 4, in some implementations, the proximal end portion 110 of the harvesting apparatus 100 comprises a bearing 112. An inner race 114i of the bearing 112 can engage the shank of the bone drill bit 20, whereas an outer race 114o of the bearing 112 can be fixed to outermost winding of the ribbon member 132. In some embodiments, the shank of the bone drill bit 20 can function as the inner race of the bearing. In some implementations, the bearing 112 configures the bone matter harvesting apparatus 100 to be rotatably coupleable with the bone drill bit 20 (e.g., by mechanically coupling with the shank of the bone drill bit 20). That is, the bearing 112 allows for the bone drill bit 20 to rotate relative to the bone matter collection apparatus 100 (other than the inner race 114i which rotates along with the bone drill bit 20). The bearing 112 allows the bone matter collection apparatus 100 to be rotatably coupled to the bone drill bit 20 such that during the drilling the bone drill bit 20 rotates faster than the bone matter collection apparatus 100. In some cases, the bone matter collection apparatus 100 will be rotationally stationary while the bone drill bit 20 rotates.

After a use of the bone drill bit 20 with the attached bone matter collection apparatus 100, the bone matter collection apparatus 100 can be detached from the bone drill bit 20 so as to access the bone matter collected inside. In some implementations, the bone matter collection apparatus 100 can be slid off proximal free end the shank of the bone drill bit 20 (after the bone drill bit 20 has been detached from the drilling device 10).

Figure 5:
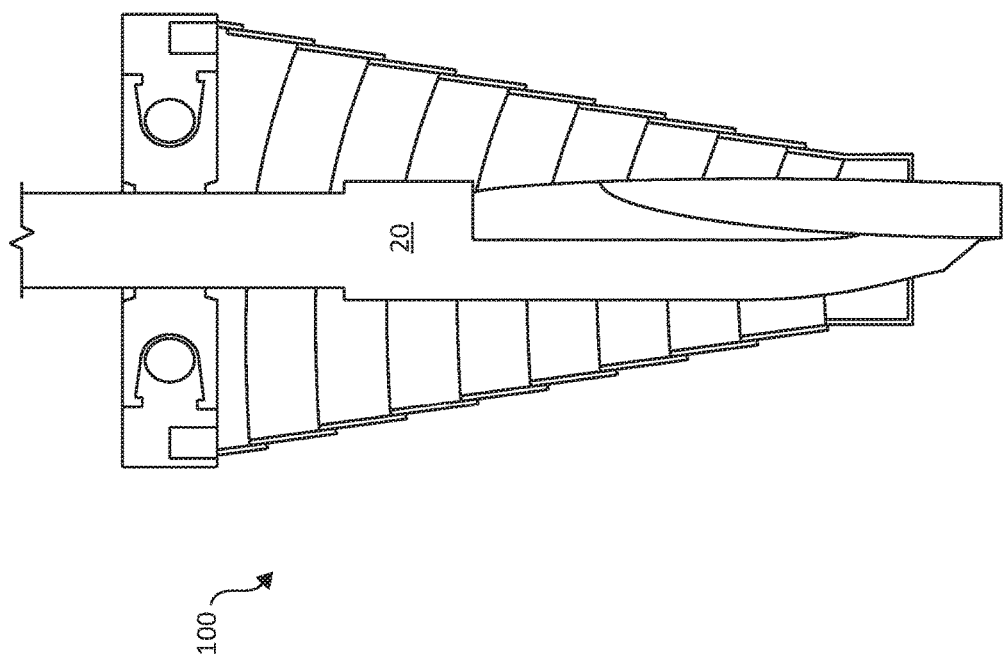
FIG. 5 shows a longitudinal cross-sectional view of the bone drill while encompassed by the bone matter collection device in a longitudinally extended configuration.

Referring to FIGS. 5 and 6, as described above the bone matter harvesting apparatus 100 is reconfigurable between a longitudinally extended configuration (FIG. 5) and a longitudinally retracted configuration (FIG. 6). The bone harvesting apparatus 100 may be retractable even farther than depicted in FIG. 6 in some implementations. In some implementations, the bone matter harvesting apparatus 100 is naturally-biased to be configured in the longitudinally extended configuration.

During drilling, the bone drill bit 20 is advanced into bone matter while the bone matter collection apparatus reconfigures toward the shorter longitudinally retracted configuration because of abutting against a surface of the bone matter. Pieces of bone matter collect inside of the bone matter harvesting apparatus 100 (e.g., within the interior region 110 as shown in FIG. 2). After such a use, the bone matter harvesting apparatus 100 can be detached from the bone drill bit 20, and the pieces of bone matter can be removed from the bone matter harvesting apparatus 100 for use or analysis.

While this specification contains many specific implementation details, these should not be construed as limitations on the scope of any invention or of what may be claimed, but rather as descriptions of features that may be specific to particular implementations of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described herein should not be understood as requiring such separation in all implementations, and it should be understood that the described program components and systems can generally be integrated together in a single product or packaged into multiple products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An apparatus for harvesting bone matter, the apparatus comprising:
   a proximal end portion defining a proximal end opening that receives a shank of a drill;
   a distal end portion defining a distal end opening through which the drill can extend; and
   an intermediate section between the proximal and distal end portions, at least a portion of the intermediate section comprising a spirally-wrapped continuous ribbon member defining a frustoconical shape,
   wherein multiple individual wraps of the spirally-wrapped continuous ribbon member overlap a portion of a distally-adjacent wrap of the spirally-wrapped continuous ribbon member and are partially overlapped by a proximally-adjacent wrap of the spirally-wrapped continuous ribbon member, and wherein the proximal end portion comprises a bearing.

2. The apparatus of claim 1, wherein the apparatus is telescopic.

3. The apparatus of claim 1, wherein the apparatus is extendable and retractable between a longitudinally extended configuration and a longitudinally retracted configuration.

4. The apparatus of claim 3, wherein the apparatus is naturally-biased to be configured in the longitudinally extended configuration.

5. The apparatus of claim 3, wherein the spirally-wrapped continuous ribbon member is longitudinally extended while the apparatus is configured in the longitudinally extended configuration and is longitudinally retracted while the apparatus is configured in the longitudinally retracted configuration.

6. The apparatus of claim 5, wherein the spirally-wrapped continuous ribbon member is naturally-biased to longitudinally extend such that the apparatus is configured in the longitudinally extended configuration.

7. The apparatus of claim 1, wherein the overlaps of adjacent wraps of the spirally-wrapped continuous ribbon member slidably increase when the apparatus reconfigures from a longitudinally extended configuration toward a longitudinally retracted configuration.

8. The apparatus of claim 1, wherein the bearing configures the apparatus to be rotatably coupleable with the drill.

9. The apparatus of claim 1, wherein the proximal end portion has a larger outer diameter than the distal end portion.

10. The apparatus of claim 1, wherein the spirally-wrapped continuous ribbon member is an elastomer.

11. The apparatus of claim 1, wherein the spirally-wrapped continuous ribbon member is metal.

12. An apparatus for harvesting bone matter, the apparatus comprising:

a proximal end portion defining a proximal end opening that receives a shank of a drill;

a distal end portion defining a distal end opening through which the drill can extend; and an intermediate section between the proximal and distal end portions, at least a portion of the intermediate section comprising a spirally-wrapped ribbon member, wherein multiple individual wraps of the spirally-wrapped ribbon member overlap a portion of a distally-adjacent wrap of the spirally-wrapped ribbon member and are partially overlapped by a proximally-adjacent wrap of the spirally-wrapped ribbon member, and wherein the proximal end portion comprises a bearing.

13. The apparatus of claim 12, wherein the spirally-wrapped ribbon member is extendable and retractable between a longitudinally extended configuration and a longitudinally retracted configuration.

14. The apparatus of claim 13, wherein the spirally-wrapped ribbon member is naturally-biased to be configured in the longitudinally extended configuration.

15. The apparatus of claim 12, wherein the overlaps of adjacent wraps of the spirally-wrapped ribbon member slidably increase when the apparatus reconfigures from a longitudinally extended configuration toward a longitudinally retracted configuration.

* * * * *